United States Patent
Nakata et al.

(10) Patent No.: US 11,559,603 B2
(45) Date of Patent: Jan. 24, 2023

(54) HIGH-STRENGTH COLLAGEN SPONGE

(71) Applicants: KOKEN CO., LTD., Tokyo (JP); OSAKA UNIVERSITY, Osaka (JP)

(72) Inventors: Ken Nakata, Osaka (JP); Gaku Kanno, Yamagata (JP)

(73) Assignees: KOKEN CO., LTD., Tokyo (JP); OSAKA UNIVERSITY, Osaka (JP)

(*) Notice: Subject to any disclaimer, the term of this patent is extended or adjusted under 35 U.S.C. 154(b) by 641 days.

(21) Appl. No.: 16/474,074

(22) PCT Filed: Dec. 21, 2017

(86) PCT No.: PCT/JP2017/045955
§ 371 (c)(1),
(2) Date: Jun. 27, 2019

(87) PCT Pub. No.: WO2018/123814
PCT Pub. Date: Jul. 5, 2018

(65) Prior Publication Data
US 2020/0121826 A1 Apr. 23, 2020

(30) Foreign Application Priority Data
Dec. 28, 2016 (JP) .............................. JP2016-254788

(51) Int. Cl.
*A61L 27/24* (2006.01)
*A61L 27/56* (2006.01)
*C08J 9/28* (2006.01)

(52) U.S. Cl.
CPC ............... *A61L 27/24* (2013.01); *A61L 27/56* (2013.01); *C08J 9/28* (2013.01); *A61L 2430/06* (2013.01); *C08J 2201/048* (2013.01); *C08J 2389/00* (2013.01)

(58) Field of Classification Search
CPC .............................. A61K 35/35; A61K 38/012
See application file for complete search history.

(56) References Cited

U.S. PATENT DOCUMENTS

| | | | |
|---|---|---|---|
| 5,256,418 A | 10/1993 | Kemp et al. | |
| 5,861,486 A * | 1/1999 | Devore | A61F 9/00819 530/356 |
| 9,993,326 B2 * | 6/2018 | Shortkroff | A61L 27/34 |
| 2003/0015825 A1 | 1/2003 | Sugie et al. | |
| 2003/0095997 A1 * | 5/2003 | Ruszczak | A61P 7/02 424/443 |
| 2005/0129730 A1 * | 6/2005 | Pang | A61L 27/56 424/423 |
| 2007/0237799 A1 * | 10/2007 | Scharnweber | A61L 27/48 530/356 |
| 2010/0093077 A1 * | 4/2010 | McClelland | C12N 5/0672 435/325 |
| 2010/0230355 A1 * | 9/2010 | Kerr | B01D 15/1892 210/198.2 |
| 2011/0293667 A1 * | 12/2011 | Baksh | A61P 19/08 435/69.1 |
| 2013/0190479 A1 * | 7/2013 | Tanaka | C07K 1/30 530/356 |
| 2014/0142200 A1 * | 5/2014 | Duan | A61L 15/325 514/773 |
| 2014/0142717 A1 | 5/2014 | Tanaka et al. | |
| 2015/0004414 A1 * | 1/2015 | Ogura | A61P 27/02 428/401 |
| 2015/0140055 A1 * | 5/2015 | Schlenoff | A61P 31/12 424/411 |
| 2016/0089474 A1 | 3/2016 | Nakata et al. | |

FOREIGN PATENT DOCUMENTS

| | | |
|---|---|---|
| EP | 0674908 A1 | 10/1995 |
| JP | 5-43734 A | 2/1993 |
| JP | 8-38592 A | 2/1996 |
| JP | 2008-79548 A | 4/2008 |
| JP | 2013-150648 A | 8/2013 |
| JP | 5909610 B2 | 4/2016 |

OTHER PUBLICATIONS

Gleason G. (2012) How to convert Centrifuge RPM to RCF or G-force (2012) https://clinfield.com/how-to-convert-centrifuge-rpm-to-rcf-or-g-force, pp. 1-5.*
Hall et al. (2013) The effect of scale and interfacial tension on liquid-liquid dispersion in inline Silverson rotor-stator mixers, chem. Eng. Res. Design, vol. 91, pp. 2156-2168.*

* cited by examiner

*Primary Examiner* — Anand U Desai
(74) *Attorney, Agent, or Firm* — Kilyk & Bowersox, P.L.L.C.

(57) ABSTRACT

To provide a collagen sponge excellent in mechanical strength and a production method for the collagen sponge. A collagen sponge including a porous construct having a pore structure, the collagen sponge having a tensile strength of 1 N or more and 5 N or less in every direction including a length direction and a width direction. The collagen sponge may be produced by a production method including the following steps: (1) a step of subjecting a collagen solution obtained by mixing collagen and a solvent to stirring and deaeration treatment; (2) a step of subjecting the collagen solution to freeze-dry treatment; and (3) a step of subjecting a dried collagen product after the freeze-dry treatment to insoluble treatment.

8 Claims, 4 Drawing Sheets

(A1)

(A2)

(B1)

(B2)

(C1)

(C2)

HIGH-STRENGTH COLLAGEN SPONGE

The present application is a National Stage Application of PCT/JP2017/045955, filed Dec. 21, 2017, which claims priority from Japanese Patent Application No. 2016-254788.

TECHNICAL FIELD

The present invention relates to a collagen sponge including a porous construct having a pore structure, and more specifically, to a collagen sponge having strong tensile strength in every direction. In addition, the present invention also relates to a production method for the collagen sponge. Further, the present invention also relates to a therapeutic method for a cartilage tissue using the collagen sponge.

BACKGROUND ART

A meniscus of a knee joint is a fibrocartilage tissue lying between a femur in the joint and a tibia of a lower leg, and is a tissue to be frequently subjected to a large mechanical load. The meniscus plays a role in shock absorption, load distribution, improvement in ability to slide, stabilization of the joint, or the like. The meniscus is often injured in sports or damaged by daily life activities, and the damage causes a pain of the knee joint and motion limitations. The meniscus is supplied with blood only at an outer peripheral portion thereof. When the portion at which blood is supplied is torn, the torn portion is healed naturally in some cases but generally needs to be treated. In addition, when a portion at which blood is not supplied is torn, the torn portion is not healed naturally and needs to be treated.

Hitherto, damaged meniscus has been treated by conservative therapy, such as drug therapy or exercise therapy, or treated by surgery, in accordance with torn sites or damage states. As the surgery treatment, excision or partial excision of the meniscus has been performed. Although, such surgery can reduce pain temporarily, functions of the meniscus remain impaired, resulting in arthrosis deformans or the like. In recent years, with an improvement in endoscopic technology, functional preservation has been performed by suture of the meniscus under arthroscopic view. However, such suture has a problem in that the suture is not applicable to damage with a defect, complex damage, degenerative tear, and the like, and hence functions of the meniscus cannot be repaired. Such problem is desired to be solved in treatment of not only the meniscus but also all cartilage tissues that are hardly healed naturally owing to a small number of blood streams.

As a solution to the problem described above, regenerative medicine has been investigated actively. For example, in Patent Literature 1, there is a disclosure of a "method involving culturing cartilage cells on a substrate (collagen sponge) for cell culture and implanting the cultured cells into a defect together with the substrate." However, in Patent Literature 1, the method involves inoculating the cells into the substrate, culturing the cells in vitro for a certain period, and then implanting the substrate into a tissue defect, and hence has a problem in that the method can be performed only in a facility with advanced equipment, such as a cell processing center. The method also has a problem of having a difficulty in ensuring safety.

In Patent Literature 2, there is a disclosure of a "collagen substrate to be used as a graft." However, in Patent Literature 2, the substrate does not have a pore structure in its surface and inside, which inhibits cell infiltration into the inside. The substrate has a small surface area to be brought into contact with a surrounding tissue and a small binding force to a tissue, and hence its bonding to an implantation site is difficult and long-term fixation with a suture thread or the like is required in order to prevent dropping thereof.

A patient to whom a substrate derived from collagen has been implanted into a tissue to be subjected to a mechanical load is required to stay in bed until the substrate is bonded to the implantation site. Therefore, a substrate to be implanted into a tissue to be subjected to a mechanical load is required to have a structure easily bonded to the implantation site and to have physical properties equivalent to those of a tissue into which the substrate is to be implanted so that a patient subjected to implantation can resume a daily life immediately. Further, the substrate is considered to be deteriorated and modified with time in vivo, and hence in order to prevent second surgery for the patient, the substrate is required to be decomposed in a certain period after implantation into a living body and replaced by a normal autologous tissue.

Collagen Meniscus Implant (ReGene Biologics Inc.) is sold as a meniscus substitute in the United States of America. The meniscus substitute uses native collagen as a raw material, and hence has a problem of low biocompatibility. ACTIFIT (trademark) (Orteq Ltd) is sold in Europe, but is formed of biodegradable polyurethane, and hence has a problem in that cells infiltrate thereinto but hardly engraft. ACTIFIT (trademark) is decomposed in about half a year to about a year after transplantation, but in a decomposed portion, the meniscus is not regenerated and a defective state remains. There is a strong need for a substitute that has high biocompatibility, and when substituted in a meniscus defective portion, allows surrounding cells to infiltrate thereinto, is decomposed over time, and allows reconstruction of a meniscus tissue along with the decomposition.

In Patent Literature 3, there is a disclosure of a "collagen sponge that has a stress of from 10 kPa to 30 kPa when loaded with 10% strain, has in its surface and inside a pore structure having an average pore diameter ranging from 50 μm to 400 μm, and has a pore diameter standard deviation equal to or less than 40% of the average pore diameter." In Patent Literature 3, there is a disclosure of a method involving adjusting a high-concentration atelocollagen solution to a neutral pH to precipitate atelocollagen fibrils, and molding the atelocollagen solution in this state into a desired shape, to thereby produce the collagen sponge. The collagen sponge of Patent Literature 3 has high compressive strength, but has weak tensile strength owing to generation of a variation in density of the dispersed state of the collagen fibrils. In addition, a collagen sponge having directionality in orientation of fibrils has high physical strength in one direction, but has weaker strength in any other direction.

In addition, a sponge-like product has been produced in the following manner: a collagen solution is concentrated, air-dried, and neutralized and warmed to produce a collagen construct having formed therein collagen fibrils, and the collagen construct is freeze-dried (Patent Literature 4). Collagen fibril formation occurs only when a pH, a temperature, and a salt concentration are adjusted to physiological conditions. The collagen sponge of Patent Literature 4 has a fibrous structure in which collagen is oriented unidirectionally.

In a tissue to be subjected to a mechanical load, such as the meniscus, a defective portion is deformed by being subjected to a force, and hence there has been a need for suture in substitution with a substitute formed of collagen. However, the substitute formed of collagen has the following problem: the substitute is markedly reduced in tensile strength when infiltrated by water in a body fluid, physiological saline, or the like, and hence suture cannot be performed because, even when the defective portion is sutured, the substitute collapses from a portion threaded with a suture thread. In surgery of the meniscus under arthroscopic view, which has been becoming mainstream in recent years, the arthroscopic view is filled with physiological saline, and when the substitute is inserted into a suture portion, the substitute is passed through an inside of a trocar (intubation) filled with physiological saline, by threading the substitute with a suture thread and pulling the suture thread. The related-art collagen sponge has not been practical because of a problem in that the related-art collagen sponge is markedly reduced in tensile strength when impregnated with water in blood, a body fluid, physiological saline, or the like, and hence cannot be passed through the inside of the trocar by pulling the sewing suture thread.

CITATION LIST

Patent Literature

[PTL 1] JP 2008-79548 A
[PTL 2] JP 08-38592 A
[PTL 3] JP 5909610 B2
[PTL 4] U.S. Pat. No. 5,256,418 A

SUMMARY OF INVENTION

Technical Problem

An object of the present invention is to provide a collagen sponge excellent in mechanical strength and a production method for the collagen sponge.

Solution to Problem

The inventors of the present invention have made investigations in order to achieve the above-mentioned object, and as a result, have found that a collagen sponge can be produced in a state in which collagen molecules are uniformly dispersed, by adjusting a collagen solution to an acidic pH and subjecting the collagen solution to stirring and deaeration, and the produced collagen sponge has a uniform pore structure and has approximately constant physical strength when a force is applied from any direction. Thus, the inventors have completed the present invention.

That is, the present invention includes the following.
1. A collagen sponge, including a porous construct having a pore structure, the collagen sponge having a tensile strength of 1 N or more and 5 N or less in any direction.
2. The collagen sponge according to the above-mentioned item 1, wherein the collagen sponge has been subjected to insoluble treatment with a chemical cross-linking agent.
3. The collagen sponge according to the above-mentioned item 1 or 2, wherein the collagen sponge has an average pore diameter falling within a range of 1 μm or more and less than 50 μm.
4. The collagen sponge according to any one of the above-mentioned items 1 to 3, wherein the collagen sponge has a stress of 7 kPa or more and 30 kPa or less when loaded with 10% strain.
5. The collagen sponge according to any one of the above-mentioned items 1 to 4, wherein the collagen sponge includes a freeze-dried product of an acidic collagen solution.
6. A collagen sponge, which is obtained by applying insoluble treatment with a chemical cross-linking agent to a porous construct having a pore structure obtained by freeze-drying a collagen solution subjected to stirring and deaeration treatment, the collagen sponge having a tensile strength of 1 N or more and 5 N or less and having a stress of 7 kPa or more and 30 kPa or less when loaded with 10% strain.
7. The collagen sponge according to the above-mentioned item 6, wherein the collagen solution includes a collagen solution obtained without undergoing a fibrillogenesis step.
8. A production method for a collagen sponge, including the following steps:
   (1) a step of subjecting a collagen solution obtained by mixing collagen and a solvent to stirring and deaeration treatment;
   (2) a step of subjecting the collagen solution to freeze-dry treatment; and
   (3) a step of subjecting a dried collagen product after the freeze-dry treatment to insoluble treatment.
9. The production method for a collagen sponge according to the above-mentioned item 8, wherein the collagen solution in the step (2) includes a collagen solution obtained without undergoing a fibrillogenesis step.
10. The production method for a collagen sponge according to the above-mentioned item 8 or 9, wherein the collagen solution has an acidic pH.
11. The production method for a collagen sponge according to any one of the above-mentioned items 8 to 10, wherein the step (1) includes the following step (1-1) and step (1-2):
   (1-1) a step of preparing a collagen solution by adding collagen to a solvent, followed by stirring and deaeration treatment; and
   (1-2) a step of subjecting the collagen solution injected into a container to stirring and deaeration treatment, to thereby reduce air bubbles in the collagen solution.
12. The production method for a collagen sponge according to any one of the above-mentioned items 8 toll, wherein the stirring and deaeration treatment is performed at a revolutional centrifugal force of 1 G or more and 600 G or less and a rotational centrifugal force of 0.1 G or more and 80 G or less.
13. A substitute for cartilage treatment, including the collagen sponge of any one of the above-mentioned items 1 to 7 as a substrate.
14. The substitute for cartilage treatment according to the above-mentioned item 13, wherein the cartilage treatment includes fibrous cartilage regeneration treatment.
15. The substitute for cartilage treatment according to the above-mentioned item 13, wherein the cartilage treatment includes meniscus regeneration treatment.
16. A therapeutic method for cartilage, including implanting the collagen sponge of any one of the above-mentioned items 1 to 7 into cartilage.
17. The therapeutic method for cartilage according to the above-mentioned item 16, wherein the cartilage includes fibrous cartilage.
18. The therapeutic method for cartilage according to the above-mentioned item 17, wherein the fibrous cartilage includes a meniscus.
19. The collagen sponge according to any one of the above-mentioned items 5 to 7, wherein the collagen solution includes an atelocollagen solution.
20. The production method for a collagen sponge according to any one of the above-mentioned items 8 to 12, wherein the collagen solution includes an atelocollagen solution.

21. The collagen sponge according to any one of the above-mentioned items 1 to 7, wherein the collagen sponge has a thickness of 1 mm or more and 10 mm or less.

Advantageous Effects of Invention

The collagen sponge of the present invention has approximately constant tensile strength in any direction, and has excellent tensile strength even under moist condition. The collagen sponge of the present invention can maintain its tensile strength even when exposed to a body fluid or water, and has such physical strength that, even when a defective portion is sutured, the collagen sponge is not broken from a portion threaded with a suture thread to fall off, and endures the suture of a tissue, thereby being able to beheld in the tissue. In addition, the collagen sponge of the present invention is also excellent in compressive strength, and hence the pore structure therein does not collapse and allows surrounding cells to infiltrate thereinto, and besides, the collagen sponge does not apply a load (physical stimulus) to a surrounding tissue when transplanted, and hence is suitable for use as a substrate for implantation into a cartilage tissue defective portion. According to the production method of the present invention, a collagen sponge having excellent physical strength can be easily produced. In addition, the production method of the present invention can deal with a large amount of an acidic solution of collagen having high viscosity and high concentration, and hence can efficiently produce a collagen sponge having a desired size.

BRIEF DESCRIPTION OF DRAWINGS

FIG. 5(A2) is an image taken of a collagen sponge obtained through a fibrillogenesis step with a scanning electron microscope (SEM) (Hitachi SU6600, 10 kV) at a magnification of 100×. FIG. 5(B1) is an image taken of the collagen sponge of the present invention with a scanning electron microscope (SEM) (Hitachi SU6600, 7 kV) at a magnification of 10, 000×. FIG. 5(B2) is an image taken of the collagen sponge obtained through a fibrillogenesis step with a scanning electronmicroscope (SEM) (Hitachi SU6600, 10 kV) at a magnification of 10,000×. FIG. 5(C1) is an image taken of the collagen sponge of the present invention with a transmission electronmicroscope (TEM) (JEOL1400Plus) at amagnification of20,000×. FIG. 5(C2) is an image taken of the collagen sponge obtained through a fibrillogenesis step with a transmission electron microscope (TEM) (JEOL 1400Plus) at a magnification of 10,000× (Reference Example 1).

DESCRIPTION OF EMBODIMENTS (Collagen Sponge)

Figure 1:
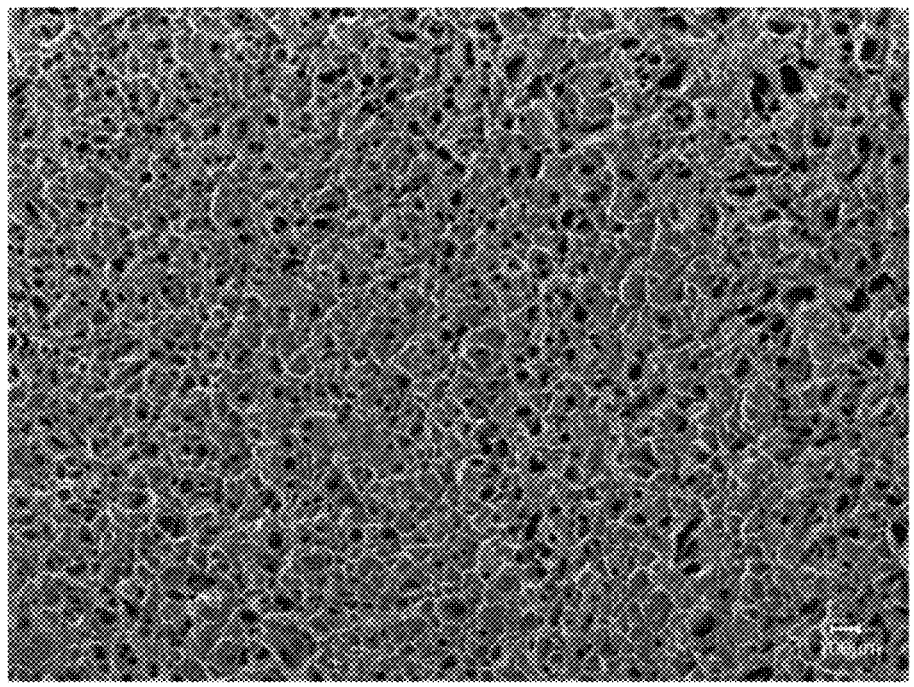
FIG. 1 is an image taken of a cross-section of a collagen sponge of the present invention with an electron microscope VHX-D510 (Keyence Corporation) at a magnification of 100×. Black portions of the image correspond to pores of the collagen sponge (Example 2).

A collagen sponge is a porous construct using collagen as a material and having a pore structure having a plurality of pores. The collagen sponge of the present invention has a tensile strength of 1 N or more and 5 N or less, which is required in the procedure of cartilage treatment. The tensile strength of the collagen sponge of the present invention is preferably 1.5 N or more and 5 N or less. The collagen sponge of the present invention has strong and excellent tensile strength in any direction. The collagen sponge of the present invention is produced by directly subjecting a collagen solution in a state in which collagen fibrils have not been formed to freeze-dry treatment, and hence the sponge is considered to be formed with collagen molecules in a random arrangement. By virtue of the collagen molecules being oriented randomly instead of being oriented in one direction, the tensile strength is excellent in any direction. When the tensile strength is less than 1 N, strength required in the suture of a tissue in cartilage treatment is not satisfied. In addition, when the tensile strength is more than 5 N, stress required in cartilage treatment (stress of 7 kPa or more and 30 kPa or less at the time of loading with 10% strain) is affected. In addition, when the tensile strength is 1 N or more and 5 N or less in any direction, the collagen sponge is not broken from a portion having a hole for a suture thread and is held in a tissue even when pulled in various directions by suture.

In addition, herein, the tensile strength is preferably tensile strength under moist condition. When the tensile strength under moist condition is 1 N or more and 5 N or less, sufficient strength and handleability can be obtained in a solution or in vivo. The tensile strength of the collagen sponge under moist condition may be evaluated by immersing the collagen sponge in physiological saline at 37° C., and then measuring its tensile strength while keeping the moist state. A test for the tensile strength may be performed by any method, and may be performed in accordance with a conventional method.

Herein, the tensile strength refers to a force (N) at break in the case where a cylindrical test piece having a diameter of 30 mm and a thickness (height) of 5 mm brought into moist condition is pulled in a radial direction. When the collagen sponge is pulled, the collagen sponge may be pulled by making holes therein and threading each of the holes with a thread. More specifically, a force (N) at break (at the time of start of breakage) in the following case is measured: two sites each 5 mm from the center on a straight line passing through the center of a smooth surface of the collagen sponge are each threaded with a suture thread, and a test piece in the state of being threaded with the suture threads is infiltrated with physiological saline, followed by pulling of the suture threads on both sides threading the test piece at a rate of 10 mm/min (see Example 2 and FIG. 3). When measured as described above, the tensile strength of the collagen sponge of the present invention is 1 N or more and 5 N or less, preferably 1.5 N or more and 5 N or less in any direction.

The collagen sponge of the present invention may be a collagen sponge that have been subjected to insoluble treatment with a chemical cross-linking agent. The insoluble treatment increases the physical strength of the collagen sponge, and extends a remaining period in a tissue into which the collagen sponge has been transplanted. The insoluble treatment cross-links collagen molecules in a random orientation, and increases the mechanical strength of the collagen sponge in all directions.

The insoluble treatment with a chemical cross-linking agent is performed by bringing the whole of a freeze-dried product of a collagen solution (hereinafter sometimes referred to as dried collagen product) into contact with the chemical cross-linking agent without deforming the dried collagen product. Examples of the chemical cross-linking agent include a water-soluble chemical cross-linking agent and a vaporable chemical cross-linking agent. The insoluble treatment with a water-soluble chemical cross-linking agent may be performed by immersing the dried collagen product in the water-soluble cross-linking agent. The insoluble treatment with a vaporable chemical cross-linking agent may be performed by placing the dried collagen product and the chemical cross-linking agent (e.g., a formalin solution) in a sealed container. The chemical cross-linking agent is preferably the water-soluble chemical cross-linking agent. Preferred water-soluble chemical cross-linking agents are as described later.

The collagen sponge of the present invention has a uniform pore structure. The average pore diameter of the collagen sponge of the present invention falls within the range of 1 µm or more and less than 50 µm, preferably the range of 5 µm or more and 30 µm or less. In addition, the pore diameter standard deviation of the collagen sponge of the present invention is 20 µm or less, preferably 15 µm or less, more preferably 7 µm or less. In the collagen sponge of the present invention, a value obtained by dividing a value of the pore diameter standard deviation by the average pore diameter (value of pore diameter standard deviation/average pore diameter) is 0.7 or less, preferably 0.6 or less. The average pore diameter and the standard deviation may be calculated by randomly selecting a plurality of (e.g., 100) pores from the surface of the collagen sponge, measuring the long diameter of each of the pores, and defining the long diameter as the diameter of the pore. The collagen sponge of the present invention has a small average pore diameter and a dense pore structure as compared to a related-art collagen sponge. The collagen sponge of the present invention has a dense and uniform pore structure, and hence can obtain a high tensile strength in any direction. When the average diameter is 1 µm or less, cells cannot infiltrate, and hence properties required in cartilage treatment are not obtained. Also when the average diameter is 50 µm or more and the standard deviation is 20 µm or more, or the value obtained by dividing the value of the pore diameter standard deviation by the average pore diameter is more than 0.7, the tensile strength and the stress become non-uniform, and hence properties required in cartilage treatment are not obtained.

The collagen sponge of the present invention has a stress of 7 kPa or more and 30 kPa or less, preferably 10 kPa or more and 25 kPa or less, more preferably 15 kPa or more and 20 kPa or less when loaded with 10% strain. The stress has the same meaning as the compressive strength. The stress at the time of loading with 10% strain is measured by immersing the collagen sponge of the present invention in physiological saline at 37° C., and using a small desktop testing machine EZ-S (Shimadzu Corporation). The collagen sponge of the present invention has both excellent tensile strength and compressive strength (stress) equivalent to that of the related-art collagen sponge. The stress required in cartilage treatment is 7 kPa or more and 30 kPa or less, and when the stress is 7 kPa or more, the pore structure for allowing cells to infiltrate can be prevented from being crushed by compression by the surrounding tissue of an implantation site. In addition, when the stress of the collagen sponge is 30 kPa or less, the stress of the collagen sponge can be prevented from being higher than that of the tissue into which the collagen sponge is to be implanted, and hence a physical stimulus to the surrounding tissue can be suppressed and prevented from causing inflammation or the like.

The collagen sponge of the present invention may be a freeze-dried product of an acidic collagen solution. The acidic collagen solution is an acidic solution in which collagen is dissolved in a solvent. A preferred pH is a pH of 1 or more and 4.5 or less, more preferably a pH of 2 or more and 4 or less, still more preferably a pH of 2.5 or more and 3.5 or less. The acidic collagen solution may contain an additive. The additive is suitably, for example, one that does not promote fibrillogenesis of the collagen. The acidic collagen solution is uniform throughout the entirety of the solution, has a uniform dispersed state of collagen molecules, and does not have collagen fibrils formed therein. The freeze-dried product of the acidic collagen solution is a product obtained by freeze-drying the acidic collagen solution, has a uniformpore structure, has more uniform compressive strength and tensile strength, and has properties of being strong against tension from any direction and being strong against compression from any direction. The freeze-dried product does not have collagen fibrils formed therein, and has collagen molecules oriented randomly instead of being oriented in one direction.

A collagen sponge according to one embodiment of the present invention is a collagen sponge obtained by applying insoluble treatment with a chemical cross-linking agent to a porous construct having a pore structure obtained by freeze-dry a collagen solution subjected to stirring and deaeration treatment, the collagen sponge having a tensile strength of 1 N or more and 5 N or less and having a stress of 7 kPa or more and 30 kPa or less when loaded with 10% strain. The collagen solution subjected to stirring and deaeration treatment is a uniform collagen solution obtained by mixing collagen and a solvent through stirring and deaeration, in which air bubbles have been reduced. Details of the stirring and deaeration treatment are described later.

The collagen solution is preferably a collagen solution obtained without undergoing a fibrillogenesis step. The collagen undergoes fibrillogenesis when a pH, a temperature, and a salt concentration are adjusted to physiological conditions. Herein, the fibrillogenesis step is a step of equilibrating the collagen solution to the physiological conditions, specifically, for example, 0.9% NaCl, phosphate buffered saline pH 7.4 (PBS), and 0.02 M $Na_2HPO_4$.

(Production Method for Collagen Sponge)

The collagen sponge of the present invention is produced by a production method including at least the following steps (1) to (3):

(1) a step of subjecting a collagen solution obtained by mixing collagen and a solvent to stirring and deaeration treatment;

(2) a step of subjecting the collagen solution to freeze-dry treatment; and (3) a step of subjecting a dried collagen product after the freeze-dry treatment to insoluble treatment.

As the collagen to be used as a material for the collagen sponge of the present invention, there may be used: insoluble collagen collected from a tissue in vivo, such as tendon collagen derived from the Achilles tendon or collagen derived from the skin; or soluble collagen or solubilized collagen, such as enzyme-solubilized collagen (atelocollagen), alkali-solubilized collagen, acid-soluble collagen, or salt-soluble collagen, and in particular, the atelocollagen is preferred. The species of animal from which the collagen is derived is not particularly limited, and any collagen having such a denaturation temperature that the collagen does not denature by heat during culture may be used without problems. Specifically, there may be used collagen derived from a mammal, such as cow or pig, collagen derived from a bird, such as chicken, or collagen derived from fish, such as tuna or tilapia. Recombinant collagen may also be used. In the collagen to be used as a material for the collagen sponge of the present invention, a side chain of a constituent amino acid of the collagen may be subjected to chemical modification. A specific example thereof is collagen subjected to acylation, such as acetylation, succinylation, or phthalation, alkylation, such as methylation or ethylation, or esterification.

The step (1) includes subjecting a collagen solution obtained by mixing collagen and a solvent to stirring and deaeration treatment. The "collagen solution obtained by mixing collagen and a solvent" only needs to be a solution in which the collagen and the solvent coexist with each other, and may be in a state immediately after mixing of the collagen and the solvent in which the collagen has not been dissolved in the solvent, or may be in a state in which the collagen has been dissolved in the solvent. The step (1) includes the following step (1-1) and/or step (1-2):

(1-1) a step of preparing a uniform high-concentration collagen solution by adding collagen to a solvent, followed by stirring and deaeration treatment;

(1-2) a step of subjecting the collagen solution injected into a container to stirring and deaeration treatment, to thereby reduce air bubbles in the collagen solution.

The step (1) preferably includes both the step (1-1) and the step (1-2).

In addition, in the present invention, in order to prevent fibrillogenesis of collagen molecules in the collagen solution to be subjected to the step (2), it is required that the collagen solution be not brought to the physiological conditions during the procedure of the step (1).

In the step (1-1), the mixture obtained by mixing the collagen and the solvent is subjected to stirring and deaeration treatment to dissolve/mix the collagen in the solvent, and thus a uniform high-concentration collagen solution can be prepared. The solvent for preparing the collagen solution may be any solvent having an acidic pH, and for example, hydrochloric acid, acetic acid, citric acid, or malic acid may be used. In addition, the collagen solution may contain an additive to the extent that the purpose of the present invention is not impaired. The additive is suitably, for example, one that does not promote fibrillogenesis of the collagen. The collagen solution prepared by subjecting the mixture to the stirring and deaeration treatment has an acidic pH. More specifically, the pH of the collagen solution is a pH of 1 or more and 4.5 or less, preferably a pH of 2 or more and 4 or less, more preferably a pH of 2.5 or more and 3.5 or less. Also in the step (1-2), the collagen solution has an acidic pH. More specifically, the pH of the collagen solution is a pH of 1 or more and 4.5 or less, preferably a pH of 2 or more and 4 or less, more preferably a pH of 2.5 or more and 3.5 or less. When the pH of the collagen solution at the time of molding is acidic, collagen molecules dissolve in the solution, the entire solution has a uniform concentration, and the dispersed state of the collagen molecules becomes a uniform state. Thus, a state in which collagen fibrils are not formed can be established. With this, the pore structure of the collagen sponge can be made more uniform, and a collagen sponge whose compressive strength and tensile strength are both more uniform can be produced. Hitherto, a high-concentration collagen solution has been adjusted to a neutral pH to precipitate collagen and used in this state for the production of a collagen sponge, but there has been a disadvantage in that the dispersed state of the collagen becomes non-uniform through the generation of a variation in density, resulting in weak tensile strength of the produced collagen sponge.

In the present invention, the collagen solution is freeze-dried to produce a dried collagen product through the step (2) to be described later. The collagen concentration of the collagen solution serving as a raw material for the freeze-dry is preferably 50 mg/ml or more and 110 mg/ml or less, 60 mg/ml or more and 100 mg/ml or less, 70 mg/ml or more and 90 mg/ml or less, or 75 mg/ml or more and 85 mg/ml or less. When the collagen concentration of the collagen solution is 50 mg/ml or more and 110 mg/ml or less, a collagen sponge having physical properties similar to those of a cartilage tissue can be obtained. Particularly when atelocollagen is used, the collagen concentration is desirably 70 mg/ml or more and 90 mg/ml or less. The use of the solution having a collagen concentration of 50 mg/ml or more and 110 mg/ml or less reduces differences in physical properties from the cartilage in vivo, and when the collagen sponge is transplanted after inoculation of cartilage cells thereinto, it is also possible to culture the inoculated cells while bearing a load to be applied to cartilage cells and a cartilage tissue in vivo. The physical strength of the collagen of the present invention may also be obtained by insoluble treatment.

In the step (1-2), the collagen solution is uniformized to reduce air bubbles in the collagen solution. The air bubbles in the collagen solution may be reduced by stirring and deaeration treatment. The collagen solution may be subjected to the stirring and deaeration treatment in a container or mold having a desired shape. The container having a desired shape is a molding container for a collagen sponge, and has a shape suited for the production of, for example, a cylindrical or cubic collagen sponge. The collagen sponge may be, after its production, used by being further cut into a desired shape at the time of actual use, or the collagen sponge may be produced using the container or mold having a desired shape in the first place. A method of using the container or mold having a desired shape in the first place is not particularly limited, but when the collagen sponge is to be transplanted into a cartilage defective portion, it is desired that the mold be produced so as to suit the shape of the cartilage defective portion. As a specific method, a mold having a shape corresponding to the shape of a defective portion may be made by optical modeling based on CT or MRI data of a patient himself.

In the present invention, the stirring and deaeration treatment is used as means for preparing a uniform high-concentration collagen solution in the step (1-1), and as means for uniformizing the collagen solution to reduce air bubbles in the solution in the step (1-2). The stirring and deaeration may be performed by using a revolution/rotation-type stirring and deaeration apparatus based on a planetary motion. The principle of the revolution/rotation-type stirring and deaeration apparatus is as follows: a container containing an object to be treated is rotated while being revolved, and thus, through the utilization of a centrifugal force action, the object to be treated is moved outward and stirred, and at the same time, deaerated by pushing out an included gas in the opposite direction. Further, because the container rotates while revolving, a spiral flow (eddy) is generated in the object to be treated in the container to increase the stirring action. A high-concentration collagen solution has high viscosity, and hence is difficult to prepare in a uniform state, but can be made uniform by performing the stirring and deaeration.

In the revolution/rotation-type stirring and deaeration apparatus, the container revolves around a predetermined revolution axis while rotating around a central axis (rotation axis). In the present invention, an angle between the plane of revolution of the container and the rotation axis is from 40 degrees to 50 degrees, preferably 45 degrees. The above-mentioned angle allows the stirring and deaeration to be performed satisfactorily. The angle may be appropriately set depending on the shape of the container and other conditions.

In the revolution/rotation-type stirring and deaeration apparatus, a revolution speed, a rotation speed, and a ratio therebetween are not particularly limited. The revolutional centrifugal force is 1 G or more and 600 G or less, preferably 400 G or more and 600 G or less. The rotational centrifugal force is 0.1 G or more and 80 G or less.

In addition, the revolutional centrifugal force, the rotational centrifugal force, and a ratio therebetween may be changed depending on the viscosity of the collagen solution. When the revolutional centrifugal force falls within the above-mentioned range, a sufficient centrifugal force can be applied to the collagen solution in the container, and hence bubbles can be efficiently removed from the collagen solution. In addition, the case in which the rotational centrifugal force falls within the above-mentioned range is preferred because the rotation of the container exhibits a high stirring effect on the collagen solution, and collagen molecules are dispersed without becoming non-uniform. When a high-concentration collagen solution is subjected to general centrifugal deaeration instead of revolution/rotation-type stirring and deaeration, a centrifugal force capable of deaeration causes the collagen molecules to be non-uniform through a centrifugal action, resulting in unevenness in collagen concentration and structure after freeze-dry.

The operation of the apparatus may be performed under the atmospheric pressure, but is preferably performed under reduced pressure in order to thoroughly perform the deaeration within a short period of time. The container is generally a tubular container, and specifically, a sterilized tubular container made of stainless steel, polyethylene, Teflon (trademark), or the like is used. A temperature during the stirring and deaeration is 4° C. or more and 40° C. or less, preferably 4° C. or more and less than 30° C. When the temperature during the stirring and deaeration is set to 40° C. or less, denaturation of the collagen can be prevented. A stirring and deaeration time greatly varies depending on the properties, such as viscosity, of the collagen solution and the shape and size of the container, but may be set to from about 1 minute to about 30 minutes in the step (1-1), and may be set to from 60 seconds to 120 seconds, preferably 90 seconds in the step (1-2). In order to suppress the generation of a concentration gradient of the collagen molecules, it is preferred that the stirring and deaeration be performed within a short period of time. For the stirring and deaeration, about 10 seconds to about 40 seconds of stirring and deaeration may be performed a plurality of times, and for example, in the case of the step (1-1), 30 seconds of stirring and deaeration treatment may be performed 10 times for a total of 5 minutes.

(Freeze-Dry Step)

The collagen solution after the stirring and deaeration is immediately freeze-dried (step (2)). The collagen solution before the freeze-dry is preferably a solution obtained without undergoing a fibrillogenesis step. Through the freeze-dry, a dried collagen product having a spongy structure is produced. A method for the freeze-dry involves first freezing the collagen solution in a molding container for a collagen sponge, and then drying the resultant under reduced pressure, and a freeze-dry technique known per se may be used. Examples of the method for the freeze-dry include rapid freezing and slow freezing. The pore size of the dried product varies depending on the freezing method, and hence a freezing method enabling a desired pore size is selected. For example, the pore size is reduced by the rapid freeze-dry, and the pore size is increased by the slow freeze-dry. The pore size is desirably such that cells can infiltrate into the inside of the collagen sponge and adhesion of the cells is not inhibited by a body fluid flowing into and out of the collagen sponge. Therefore, the pore size is desirably adjusted so as to achieve an average pore diameter of 1 μm or more and less than 50 μm, preferably 5 μm or more and 30 μm or less. In the drying under reduced pressure, the boiling point of the frozen product is lowered by the reduced pressure, and the inside of the frozen product is dried by subliming the water in the frozen product at a low temperature. In the present invention, the drying under reduced pressure may be performed by setting a starting temperature to from −40° C. to −15° C., and increasing the temperature to normal temperature over time. Specifically, the desired pore size may be obtained by leaving a container filled with the collagen solution to stand still in a freeze-dry machine cooled to −30° C. to freeze the solution, and then drying the resultant under reduced pressure for from 70 hours to 75 hours while increasing the temperature over time from −30° C. to normal temperature.

(Insoluble Treatment Step)

In the present invention, the step (3), i.e., insoluble treatment of the dried collagen product can increase the physical strength of the dried collagen product, and adjust the remaining period of the collagen sponge in a tissue into which the collagen sponge has been transplanted. When the insoluble treatment is performed, the insoluble treatment needs to be performed uniformly into an inside of the dried collagen product without deforming the dried collagen product. The insoluble treatment in the present invention is desirably treatment with a chemical cross-linking agent, dry-heat treatment, or γ-ray irradiation treatment, which enables insoluble treatment into the inside of the dried product. Examples of the chemical cross-linking agent include a water-soluble chemical cross-linking agent and a vaporable chemical cross-linking agent. It is considered that the insoluble treatment can cross-link collagen in a random orientation, and can increase the mechanical strength of the collagen sponge.

Reaction conditions for each insoluble treatment are adjusted so that the finished product has a tensile strength of 1 N or more and 5 N or less and has a stress of 7 kPa or more and 30 kPa or less when loaded with 10% strain. The dry-heat treatment may be performed by achieving a completely dried state and then leaving the dried product to stand for 30 minutes or more under a heating atmosphere of about 120° C. The γ-ray irradiation treatment may be performed by giving moisture to the dried product to the extent that the product is not swollen and then performing irradiation at 0.1 kGy or more. The insoluble treatment with a water-soluble chemical cross-linking agent may be accomplished by immersing the dried collagen product in an aqueous solution containing the water-soluble chemical cross-linking agent. For example, when glutaraldehyde is used, the dried collagen product is immersed in an aqueous solution containing glutaraldehyde at a concentration of 0.5%. In addition, in the insoluble treatment with a vaporable chemical cross-linking agent, the insoluble treatment maybe performed in a sealed container by placing the dried collagen product and the chemical cross-linking agent, such as a formalin solution, in the sealed container. The water-soluble chemical cross-linking agent is, for example, an aldehyde compound or an epoxy compound, more preferably an epoxy compound. Specifically, there may be used, for example, ethylene glycol diglycidyl ether, allyl glycidyl ether, 2-ethylhexyl glycidyl ether, phenyl glycidyl ether, phenol (EO) 5 glycidyl ether, p-tert-butylphenyl glycidyl ether, dibromophenyl glycidyl ether, lauryl alcohol (ED) 15 glycidyl ether, resorcinol diglycidyl ether, neopentyl glycol diglycidyl ether, 1,6-hexanediol diglycidyl ether, glycerin polyglycidyl ether, trimethylolpropane polyglycidyl ether, pentaerythritol polyglycidyl ether, diglycerin polyglycidyl ether, polyglycerin polyglycidyl ether, sorbitol polyglycidyl ether, diglycidyl terephthalate, diethylene glycol diglycidyl ether, polyethylene glycol diglycidyl ether, or polybutadiene diglycidyl ether. Of those, ethylene glycol diglycidyl ether is most preferred. The dried collagen product is immersed in an ethylene glycol diglycidyl ether-containing solution, followed by deaeration under reduced pressure (1 minute to 1 hour) and subsequent stirring (1 hour to 48 hours). After that, the product is subjected to washing with an ion exchange water and neutralization of an unreacted group with a neutralizing solution, and then dried.

In the present invention, the insoluble treatment is performed so that the physical strength, in particular, stress of the collagen sponge is equivalent to that of a cartilage tissue. In daily life, the cartilage tissue has a deformation ratio (strain) of about 10% when compressed in a vertical direction and has a stress under the condition of from 7 kPa to 30 kPa. Therefore, conditions for the insoluble treatment are adjusted so that the stress of the substrate of the present invention is also from 7 kPa to 30 kPa when loaded with 10% strain. The collagen sponge of the present invention has biocompatibility, but the insoluble treatment also provides an effect of preventing early decomposition and absorption of the substrate in vivo.

(Applications of Collagen Sponge)

The collagen sponge of the present invention may be used for cartilage treatment. The collagen sponge of the present invention is suited for being implanted into a living body as a reinforcement agent or substitute for a cartilage tissue. The collagen sponge of the present invention may be implanted as it is into a living body, or may be implanted after cells have been inoculated thereinto and cultured prior to the implantation. In the culture, the cells may be cultured while a load similar to that to be applied to a cartilage tissue of a living body is applied. The collagen sponge of the present invention has tensile strength and compressive strength (stress) equivalent to those of a cartilage tissue into which the collagen sponge is to be implanted, and has no unevenness in structure and strength, and hence can reduce a mechanical load to be applied to a tissue around the tissue into which the collagen sponge is implanted, and can also maintain a pore structure for allowing cells to infiltrate thereinto.

A method of treating a joint using the collagen sponge of the present invention is not particularly limited, but an example thereof is described below. First, small holes (e.g., at two or three sites) are made in a skin surface surrounding a joint in need of treatment, and a trocar is inserted into the joint. Insides of the joint and the trocar are filled with physiological saline, and an endoscope is passed through the inside of the trocar to gain direct access to a surgical site. A substitute (also called a reinforcement agent) containing the collagen sponge is threaded with a suture thread and soaked in physiological saline. Under the state in which the substitute is immersed in physiological saline, the substitute is passed through the inside of the trocar to be transported into the joint by pulling the suture thread of the substitute. The substitute is implanted into the damaged site of the cartilage tissue of the joint, and is sewn with the suture thread. After that, the trocar and the endoscope are removed from the joint, and the holes in the skin surface are closed.

The collagen sponge of the present invention may be used for the substitution of cartilages throughout the body, such as articular cartilage, epiphyseal cartilage, laryngeal cartilage, nasal cartilage, costal cartilage, tracheal/bronchial cartilage, articular disc, articular meniscus, articular lip, intervertebral disc, pubic cartilage, auricle, ear canal, and epiglottic cartilage. Examples of the cartilage include fibrous cartilage, hyaline cartilage, and elastic cartilage. The collagen sponge of the present invention is preferably used for the substitution of fibrous cartilage formed by overlapping fibril components. Examples of the fibrous cartilage include sacroiliac joint, temporomandibular joint, sternoclavicular joint, intervertebral disc, pubic symphysis, articular meniscus, and articular disc. The articular cartilage is a tissue to be subjected to a mechanical load, and a general therapeutic method for treating a cartilage defect is transplantation of autologous cartilage, substitution of a fibrin clot, excision of a damaged part, transplantation of an artificial joint, medication, no treatment, or the like. The collagen sponge of the present invention has high biocompatibility, and hardly causes an antigen-antibody reaction when transplanted. In addition, the collagen sponge of the present invention is decomposed by phagocytes or the like to disappear in a certain period of time. When substituted in a defective portion of cartilage, in particular, a meniscus defective portion, the substitute allows surrounding cells to infiltrate thereinto, is decomposed over time, and allows the reconstruction of the tissue along with the decomposition. The cells that have infiltrated into the collagen sponge secrete an ex vivo matrix to regenerate the tissue. Even after the decomposition of the collagen sponge, the cells and the secreted matrix remain, resulting in a state in which the tissue has been regenerated.

The collagen sponge of the present invention is particularly suited for use as a reinforcement agent for a meniscus. The meniscus is a tissue sandwiched between the articular cartilages of a femur and a tibia, is subjected to strong forces from above and below, and changes its shape in response to the forces. When merely press-fitted to a defective portion of the meniscus, a substitute formed of a collagen sponge falls off, and hence suture is required. The collagen sponge of the present invention can maintain its tensile strength even when exposed to a body fluid or water, and has such physical strength that, even when the defective portion is sutured, the collagen sponge is not broken from a portion threaded with a suture thread to fall off, and can endure the suture of the tissue. That is, the collagen sponge of the present invention can be used as a substitute in treatment involving reconstructing the meniscus (suture or substitution). The collagen sponge of the present invention is also excellent in compressive strength, and hence the pore structure therein does not collapse and allows surrounding cells to infiltrate thereinto, and besides, the collagen sponge does not apply a load (physical stimulus) to a surrounding tissue when transplanted into the meniscus.

A human meniscus has a crescent shape having a length of about 40 mm, a width of about 8 mm, and a thickness of from 1 mm to 4 mm. The meniscus is a tissue whose outer edge has fibrils oriented from an anterior horn toward a posterior horn and is strong against a force applied outward from the center, and whose inner edge is strong against compression. Hitherto, the reconstruction of a totally removed or totally absent meniscus has involved using an autologous tendon for the outer edge and leaving the inner edge untreated because of the unavailability of a substitute having strength capable of enduring compression. The collagen sponge of the present invention is particularly preferably used as a substitute for substitution for the total removal, total absence, subtotal removal, or partial absence of the inner edge. The substitute for the inner edge needs to have a maximum size of a length of 30 mm. The collagen sponge of the present invention can provide a substitute that, even when having a size of a length of 30 mm, has high biocompatibility, has a uniformpore structure and uniform compressive strength, and has tensile strength allowing suture. The collagen sponge of the present invention may be used for surgery under arthroscopic view. The collagen sponge of the present invention has strength capable of enduring suture even when impregnated with water in blood, a body fluid, physiological saline, or the like. In the surgery under arthroscopic view, the collagen sponge of the present invention can be passed through the inside of a trocar by threading the collagen sponge infiltrated with physiological saline with a suture thread and pulling the suture thread, and can be sutured to a tissue in the state of being immersed in physiological saline.

The collagen sponge of the present invention is particularly suited for the treatment of the meniscus among cartilage tissues. Therefore, it is important that the shape of the collagen sponge have a thickness (height) of 1 mm or more and 10 mm or less, preferably 3 mm or more and 5 mm or less. It is preferred that the shape of the collagen sponge have a length of 1 mm or more and 50 mm or less, preferably 5 mm or more and 30 mm or less, and a width of 1 mm or more and 50 mm or less, preferably 5 mm or more and 30 mm or less. In addition, the collagen sponge of the present invention can be cut/processed so as to have a shape matching the size of a defect of each tissue, and hence does not entail an operation such as joining of a plurality of substitutes together. When the collagen sponge of the present invention is used for substitution for the total removal, total absence, subtotal removal, or partial absence of the meniscus, the collagen sponge preferably has a disc shape or a crescent shape. When the collagen sponge of the present invention is used for regeneration treatment of the meniscus, it is considered that the collagen sponge allows the meniscus to be repaired to its original size, and hence the risk of developing knee osteoarthritis can be reduced.

The collagen sponge of the present invention may also be used for regeneration treatment of an intervertebral disc.

In addition, the collagen sponge of the present invention may be not only applied to hitherto performed cartilage treatment, but also used for cartilage treatment to be developed in the future, in particular, meniscus regeneration treatment or intervertebral disc regeneration treatment.

The present invention is described by way of Examples below. However, the present invention is by no means limited to these Examples.

EXAMPLE 1

[Production of Collagen Sponge of the Present Invention]

(1) Enzyme-solubilized collagen (atelocollagen) derived from bovine skin was added to hydrochloric acid, and further, the mixture was subjected to stirring and deaeration using Awatori Rentaro (trademark) ARE-310 (Thinky Corporation) at a revolutional centrifugal force of 420 G and a rotational centrifugal force of 25 G for 5 minutes (30 seconds×10 times) to provide an acidic collagen solution (pH 3). The stirring and deaeration was divided into 10 times so as to prevent an increase in temperature of the collagen solution. In this Example, the operation of the stirring and deaeration was stopped every 30 seconds, and the temperature of the collagen solution was monitored and confirmed not to be more than 30° C. The collagen concentration in the solution was measured by the Kjeldahl method, and the collagen concentration in the solution was adjusted to 80 mg/ml. When the concentration was less than 80 mg/ml, the concentration was increased by adding enzyme-solubilized collagen.

7 ml of the collagen solution having a collagen concentration of 80 mg/ml was dispensed into a cup made of polyacetal, and further, was subjected to stirring and deaeration treatment using Awatori Rentaro (trademark) ARE-310 (Thinky Corporation) at a revolutional centrifugal force of 516 G and a rotational centrifugal force of 0.14 G (deaeration mode, 2,200 rpm) for 90 seconds.

(2) After the stirring and deaeration, the cup having the collagen solution dispensed therein was left to stand still on a shelf and cooled from room temperature to −20° C. to freeze the collagen solution, and then dried under reduced pressure for 73 hours while the temperature was increased over time from −30° C. to normal temperature.

(3) The dried collagen product after the completion of the freeze-dry was removed from the cup made of polyacetal, cut to a required thickness, and then subjected to insoluble treatment by placing the dried collagen product in a container made of PP containing ethylene glycol diglycidyl ether serving as a cross-linking agent, and performing deaeration under reduced pressure (10 minutes to 20 minutes), followed by stirring (30° C., 18 hours), so that the finished product had a tensile strength of 1 N or more and 5 N or less and had a stress of 7 kPa or more and 30 kPa or less when loaded with 10% strain.

Next, the collagen sponge after the insoluble treatment was transferred to a container made of PP containing ion exchange water, and stirred (30° C., 30 minutes×10 times to 15 times). After that, a neutralizing solution for the cross-linking agent was added, and the mixture was stirred (30° C., 18 hours), transferred again to a container made of PP containing ion exchange water, and stirred (30° C., 30 minutes×10 times to 15 times). Thus, washing was performed. Finally, the resultant was dried to provide a collagen sponge of the present invention.

As Comparative Example, on the basis of a method described in Patent Literature 3, a collagen dispersion obtained by dispersing collagen in purified water was centrifuged at 760 G for 20 minutes instead of stirring and deaeration treatment, and then subjected to freeze-dry and insoluble treatment to produce a related-art collagen sponge.

EXAMPLE 2

[Confirmation of Pore Structure and Physical Strength of Collagen Sponge]

A scanning electron microscope image (SEM image), tensile strength, and compressive strength were confirmed for each of the collagen sponge of the present invention produced in Example 1 and the related-art collagen sponge.

Figure 2:
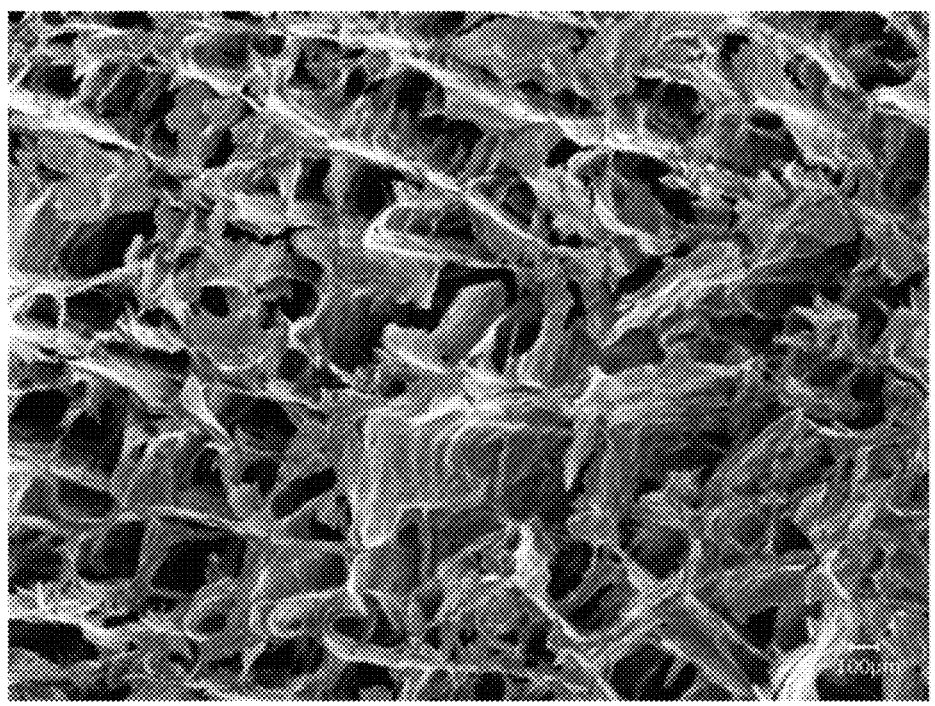
FIG. 2 is an image taken of a cross-section of a related-art collagen sponge with an electron microscope VHX-D510 (Keyence Corporation) at a magnification of 100×. Black portions of the image correspond to pores of the collagen sponge (Example 2).

(1) A cross-section of each of the collagen sponge of the present invention and the related-art collagen sponge was observed with a scanning electron microscope. The cross-section of the collagen sponge of the present invention is shown in FIG. 1 (scanning electron microscope image, Bar: 100 µm), and the cross-section of the related-art collagen sponge is shown in FIG. 2. As apparent from FIG. 1, the structure of the surface of the collagen sponge of the present invention was uniform, and a dense pore structure was found. Meanwhile, the surface of the related-art collagen sponge was uniform, but individual pores thereof were large as compared to those of the collagen sponge of the present invention, and it was found that a portion in which collagen was present and a portion in which collagen was absent (pore) were distinct from each other.

Further, the diameters of the pores on the surface (scanning electron microscope image) of each of the collagen sponge of the present invention and the related-art collagen sponge were measured. One pore was selected randomly from the surface of the collagen sponge, the long diameter of the pore was measured, and the long diameter was defined as the diameter of the pore. The procedure was performed for 100 pores, and the average pore diameter and pore diameter standard deviation were calculated.

The collagen sponge of the present invention was found to have an average pore diameter of 11.85 µm and a pore diameter standard deviation of 5.89 µm. The related-art collagen sponge was found to have an average pore diameter of 52.96 µm and a pore diameter standard deviation of 24.22 µm. In addition, the collagen sponge of the present invention was produced by the same technique as in Example 1, and the diameters of the pores thereof were measured in the same manner as in this Example and found to be 9.97 µm±4.85 and 15.01 µm±6.99. Meanwhile, the related-art collagen sponge was produced in the same manner as the one described as Comparative Example in Example 1, and the diameters of the pores thereof were measured and found to be 42.08 µm±15.86 and 72.64 µm±35.33. Thus, it was confirmed that the pores of the collagen sponge of the present invention had smaller sizes than those of the related-art collagen sponge.

(2) The stresses of the collagen sponge of the present invention and the related-art collagen sponge were measured. By referring to the deformation degree (10% strain) of the meniscus by a load to be applied to the knee in daily life, the stress was measured when a scaffold was compressed with 10% strain. The stress was measured for the collagen sponge of the present invention immersed in physiological saline at 37° C. using a small desktop testing machine EZ-S (Shimadzu Corporation).

As a result, the collagen sponge of the present invention was found to have a stress of about 10 kPa when loaded with 10% strain. The related-art collagen sponge was found to have unevenness in many parts and have a stress of about 18.7 kPa when loaded with 10% strain in a certain part.

Figure 3:
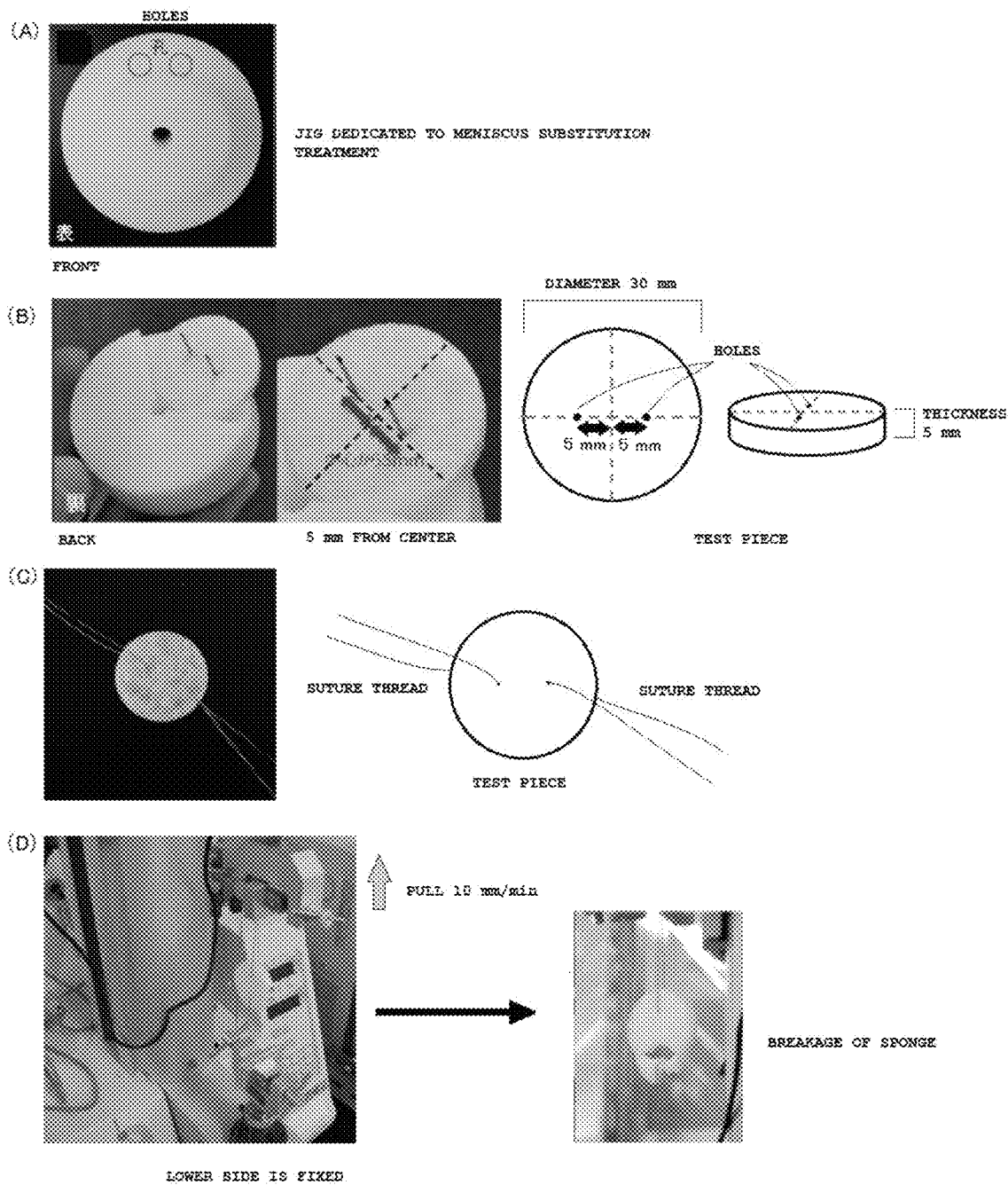
FIG. 3 are explanatory views of a method of measuring the tensile strength of a collagen sponge (Example 2).

(3) In accordance with the method described in FIG. 3, the tensile strength of each of the collagen sponge of the present invention and the related-art collagen sponge was measured. First, a cylindrical collagen sponge test piece having a diameter of 30 mm and a thickness (height) of 5 mm was prepared. Two sites each 5 mm away from the center on a straight line passing through the center of a smooth surface of the test piece were each threaded with a suture thread (No. 2-0). The test piece in the state of being threaded with the suture threads was immersed in physiological saline. The test piece was placed in a desiccator, a vacuum pump was connected thereto, and degassing was performed for 3 minutes. The suture threads on both sides threading the test piece were fixed to a small desktop testing machine EZ-S (Shimadzu Corporation) and pulled at a rate of 10 mm/min, and a force (N) at break (at the time of start of breakage) in this case was measured. The thickness of the test piece was measured with a Vernier caliper.

Figure 4:
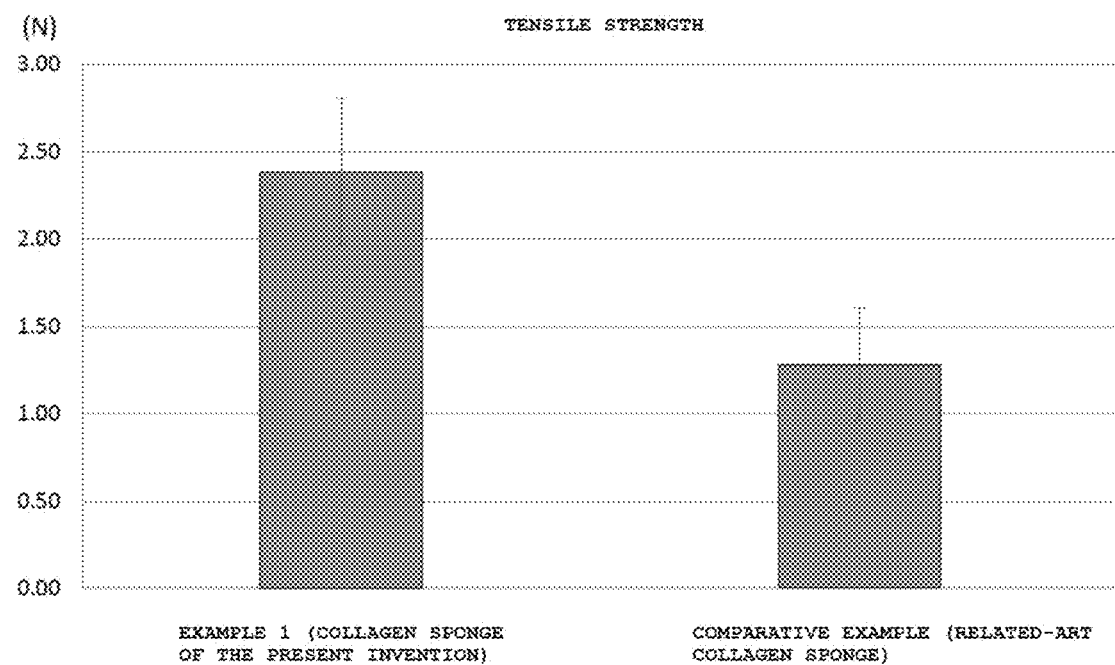
FIG. 4 is a graph for showing the results of measurement of the tensile strength of the collagen sponge of the present invention and the tensile strength of the related-art collagen sponge (Example 2).

The results are shown in FIG. 4 and Table 1 below. All 51 test pieces of the collagen sponge of the present invention had a tensile strength of 1.5 N or more, and hence it was confirmed that the tensile strength was strong in all directions. Meanwhile, the related-art collagen sponge had a mean value for tensile strength lower than that of the collagen sponge of the present invention, and a minimum value for tensile strength of 0.79 N, and hence it was shown that tensile strength required in cartilage treatment was not satisfied in some directions.

TABLE 1

| | Tensile Strength | |
|---|---|---|
| | Example 1 | Comparative Example |
| Mean value (N) | 2.39 | 1.29 |
| Standard deviation value (N) | 0.42 | 0.32 |
| Maximum value (N) | 3.43 | 1.95 |
| Minimum value (N) | 1.54 | 0.79 |
| Number of samples | n = 51 | n = 14 |

EXAMPLE 3

[Experiment on Implantation of Collagen Sponge into Living Body]

The collagen sponge of the present invention produced in Example 1 was implanted into miniature pigs, and was evaluated for efficacy and safety in meniscus defect repair. A 3 mm×8 mm defect was produced in a region in front of the medial meniscus ranging to the medial joint of each of eight knees of eight 10- to 12-month-old miniature pigs, and a substituted group of four knees each fitted with the collagen sponge having the same size as the defective portion and a non-substituted group of four knees were comparatively investigated 6 months after surgery. Quantitative evaluations based on scores were performed through macroscopic observation for tissue repair at the defective portion, cartilage damage, and the presence or absence of synovial membrane hyperplasia, and through histological observation for the repaired tissue amount of the defective portion, a repaired tissue image, safranin O stainability, a meniscus surface shape, a meniscus inner shape, and adhesion to a surrounding tissue.

The results were as described below. In the substituted group with the collagen sponge of the present invention, tissue repair was significantly satisfactory in the macroscopic observation. No significant difference in cartilage damage or synovial membrane hyperplasia was found between the two groups. In the histological observation, the substituted group with the collagen sponge of the present invention was significantly satisfactory. In view of this, it was considered that the treatment for repairing a meniscus defect in miniature pigs with the collagen sponge of the present invention was safe and efficacious.

REFERENCE EXAMPLE 1

A structural difference between a collagen sponge obtained without undergoing a fibrillogenesis step and a collagen sponge obtained through a fibrillogenesis step was confirmed.

The product of the present invention was used as the collagen sponge obtained without undergoing a fibrillogenesis step.

The collagen sponge obtained through a fibrillogenesis step was produced as described below. Enzyme-solubilized collagen (atelocollagen) derived from bovine skin was added to hydrochloric acid to prepare a collagen solution (11.0 mg/mL, pH 3.0). The collagen solution was filtered through a membrane filter (pore size: 1 µm) (maximum air pressure: 4 atom). After that, the collagen solution obtained by the filtration was neutralized to be gelled (fibrillogenesis). Specifically, the collagen solution was poured into a 10 cm×10 cm tray to a height of 1 cm. The tray was left to stand still in a sealed container (capacity: 1 L), and the inside of the container was filled with an ammonia gas for neutralization. After 1 hour, the tray containing the collagen gel obtained through fibrillogenesis was removed from the container. The resultant collagen gel was subjected to freeze-dry and insoluble treatment to produce a collagen sponge.

Figure 5:
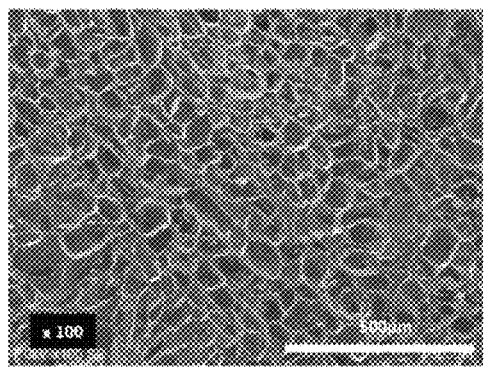
FIG. 5(A1) is an image taken of the collagen sponge of the present invention with a scanning electron microscope (SEM) (Hitachi SU6600, 7 kV) at a magnification of 100×.
Figure 5:
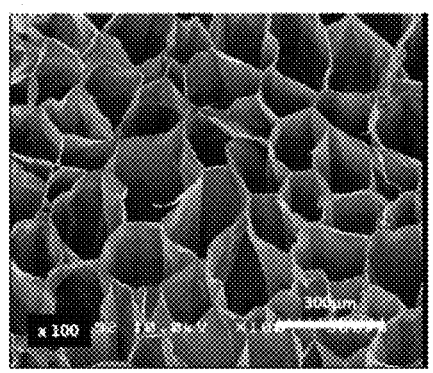
Figure 5:
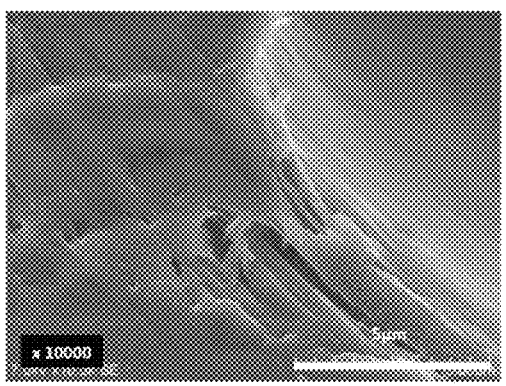
Figure 5:
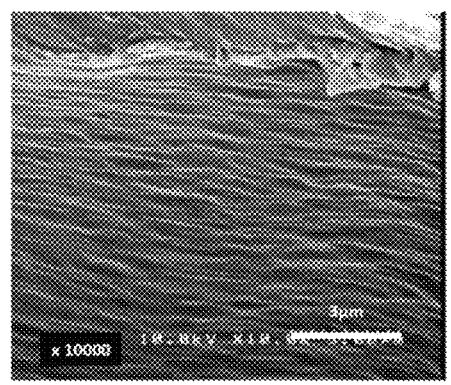
Figure 5:
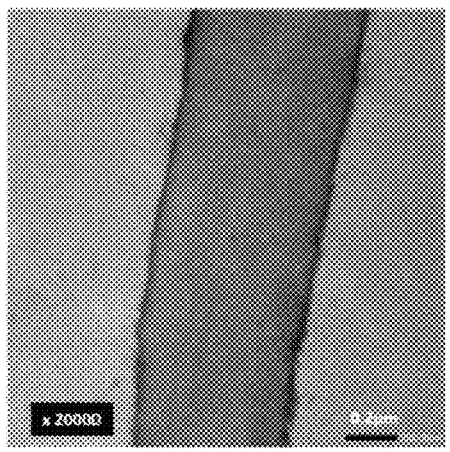
Figure 5:
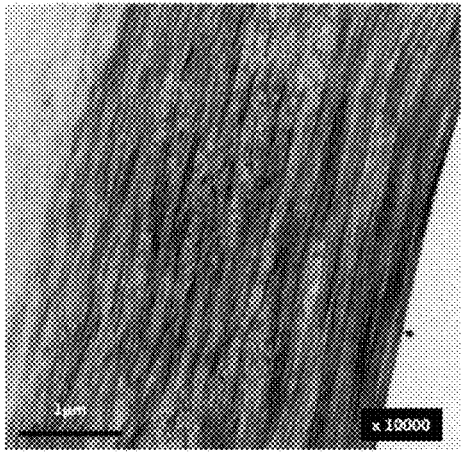

The collagen sponge obtained without undergoing a fibrillogenesis step (product of the present invention) and the collagen sponge obtained through a fibrillogenesis step were observed with a scanning electron microscope (SEM) and a transmission electron microscope (TEM) (FIG. 5). The collagen sponge obtained through a fibrillogenesis step was found to have surface irregularities, and confirmed to have a unidirectional fibrillar structure. Meanwhile, the collagen sponge obtained without undergoing a fibrillogenesis step had a smooth surface, and, was not found to have a fibrillar structure.

INDUSTRIAL APPLICABILITY

The collagen sponge of the present invention has approximately constant tensile strength in any direction, and has excellent tensile strength even under moist condition. In addition, the collagen sponge of the present invention is also excellent in compressive strength, and hence is suitable for use as a substrate for implantation into a cartilage tissue defective portion. In surgery under arthroscopic view, the collagen sponge of the present invention can be passed through the inside of a trocar by threading the collagen sponge infiltrated with physiological saline with a suture thread and pulling the suture thread, and can be sutured to a tissue in the state of being immersed in physiological saline. In addition, the collagen sponge of the present invention is useful because it is considered that the collagen sponge allows a meniscus to be repaired to its original size, and hence the risk of developing knee osteoarthritis can be reduced. Further, the collagen sponge of the present invention has physical strength that has heretofore been impossible to achieve, and hence the collagen sponge of the present invention is also expected to be used in the development of novel cartilage reconstruction treatment.

The invention claimed is:

1. A production method for a collagen sponge, comprising the following steps:
   (1) a step of subjecting a collagen solution obtained by mixing collagen and a solvent to stirring and deaeration treatment;
   (2) a step of subjecting the collagen solution to freeze-dry treatment; and
   (3) a step of subjecting a dried collagen product after the freeze-dry treatment to an insoluble treatment,
   wherein the collagen solution in the step (2) comprises a collagen solution obtained without undergoing a fibrillogenesis step.

2. The production method for a collagen sponge according to claim 1, wherein the collagen solution has an acidic pH.

3. The production method for a collagen sponge according to claim 1, wherein the step (1) includes the following step (1-1), step (1-2), and step (1-3):
   (1-1) a step of preparing a collagen solution by adding collagen to a solvent, followed by stirring and deaeration treatment;
   (1-2) a step of injecting the collagen solution into a container; and
   (1-3) a step of subjecting the collagen solution injected into the container to stirring and deaeration treatment, to thereby reduce air bubbles in the collagen solution.

4. The production method for a collagen sponge according to claim 1, wherein the stirring and deaeration treatment is performed at a revolutional centrifugal force of 1 G or more and 600 G or less and a rotational centrifugal force of 0.1 G or more and 80 G or less.

5. The production method for a collagen sponge according to claim 1, wherein the collagen solution in the step (1) to (3) comprises a collagen solution obtained without undergoing a fibrillogenesis step.

6. The production method for a collagen sponge according to claim 1, wherein the collagen sponge does not contain collagen fibrils.

7. The production method for a collagen sponge according to claim 1, wherein the collagen sponge is formed with collagen molecules in a random arrangement.

8. The production method for a collagen sponge according to claim 1, wherein the deaeration treatment is performed using a revolution/rotation-type stirring and deaeration apparatus.

* * * * *